(12) United States Patent
Kitano et al.

(10) Patent No.: US 11,459,407 B2
(45) Date of Patent: Oct. 4, 2022

(54) CHEMICALLY MODIFIED CELLULOSE FIBER AND METHOD FOR PRODUCING THE SAME

(71) Applicant: DAI-ICHI KOGYO SEIYAKU CO., LTD., Kyoto (JP)

(72) Inventors: Yuka Kitano, Kyoto (JP); Masayuki Hashimoto, Kyoto (JP)

(73) Assignee: DAI-ICHI KOGYO SEIYAKU CO., LTD., Kyoto (JP)

( * ) Notice: Subject to any disclaimer, the term of this patent is extended or adjusted under 35 U.S.C. 154(b) by 0 days.

(21) Appl. No.: 16/620,986

(22) PCT Filed: May 30, 2018

(86) PCT No.: PCT/JP2018/020727
§ 371 (c)(1),
(2) Date: Dec. 10, 2019

(87) PCT Pub. No.: WO2019/003774
PCT Pub. Date: Jan. 3, 2019

(65) Prior Publication Data
US 2020/0190221 A1    Jun. 18, 2020

(30) Foreign Application Priority Data

Jun. 29, 2017  (JP) ............................. JP2017-127903

(51) Int. Cl.
*C08B 5/14* (2006.01)
*D01F 2/28* (2006.01)

(52) U.S. Cl.
CPC . *C08B 5/14* (2013.01); *D01F 2/28* (2013.01)

(58) Field of Classification Search
CPC ..................................................... C08B 5/14
See application file for complete search history.

(56) References Cited

U.S. PATENT DOCUMENTS

| 2,511,229 A | 6/1950 | Cunningham et al. | |
| 4,377,648 A | 3/1983 | Menault et al. | |
| 6,800,754 B1 | 10/2004 | Chauvelon et al. | |
| 9,056,792 B2* | 6/2015 | Weerawarna | ........... C04B 28/02 |
| 2016/0074289 A1* | 3/2016 | Hayashi | ................ A61K 8/733 |
| | | | 424/401 |

FOREIGN PATENT DOCUMENTS

| CN | 102863544 A | 1/2013 |
| JP | 56-53145 A | 5/1981 |
| JP | 2007-231433 A | 9/2007 |

OTHER PUBLICATIONS

Japanese Office Action dated Aug. 7, 2018 in Japanese Patent Application No. 2017-127903 (with English translation), 11 pages.
Combined Chinese Office Action dated Mar. 39, 2021 in Chinese Patent Application No. 201880041108.1 (with English translation), 12 pages.
European Search Report Opinion dated Feb. 25, 2021 in European Application No. 18824707.6, 3 pages.
Isogai, A., et al., "TEMPO-oxidized cellulose nanofibers", Nanoscale, vol. 3, 2011, pp. 71-85.
Office Action dated Nov. 19, 2021 in corresponding Chinese Patent Application No. 201880041108.1 (with English-language Translation), 14 pages.
International Search Report dated Aug. 7, 2018 in PCT/JP2018/020727, 2 pages.
English translation of Written Opinion of the International Searching Authority dated Aug. 7, 2018 in PCT/JP2018/020727, 8 pages.
Petropvlovskiy, G. A. et al., "Effect of Preliminary Crosslinking on Sulfation Reaction of Cellulose" Zh Prikl Khim, vol. 58, No. 2, 1985, pp. 421-423.

\* cited by examiner

*Primary Examiner* — Shaojia A Jiang
*Assistant Examiner* — Everett White
(74) *Attorney, Agent, or Firm* — Oblon, McClelland, Maier & Neustadt, L.L.P.

(57) ABSTRACT

A sulfated cellulose fiber having a cellulose I crystal structure is provided.

A chemically modified cellulose fiber which has a cellulose I crystal and in which some hydroxyl groups of cellulose are substituted with a substituent represented by formula (1). An amount of the substituent introduced is 0.1 mmol to 3.0 mmol per 1 g of the chemically modified cellulose fiber, and an average degree of polymerization is 350 or more. (In formula (1), M represents a monovalent to trivalent cation.) In the production of the chemically modified cellulose fiber, a cellulose fiber is treated with sulfamic acid while maintaining a cellulose fiber shape to allow sulfamic acid and a cellulose fine fiber which is a constituent of the cellulose fiber to react with each other.

[Chem. 1]

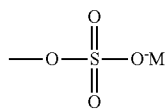

(1)

20 Claims, 1 Drawing Sheet

CHEMICALLY MODIFIED CELLULOSE FIBER AND METHOD FOR PRODUCING THE SAME

TECHNICAL FIELD

The present invention relates to a chemically modified cellulose fiber and a method for producing the same.

BACKGROUND ART

Cellulose fibers are used as industrial raw materials of food, cosmetics, functional paper, resin reinforcing materials, and the like. Furthermore, chemically modified cellulose fibers produced by chemically modifying surfaces of cellulose fibers have bright prospects because such chemically modified cellulose fibers are easily dispersed in water and thus are applicable to a wide range of industrial raw materials.

An example of chemically modified cellulose is sulfated cellulose. An example thereof is granular sulfated cellulose obtained by subjecting cellulose to sulfation using sulfuric acid anhydride as a sulfating reagent (for example, Patent Literature 1). There is also disclosed a technique for producing sulfated cellulose having a degree of polymerization of 60 or less and having the cellulose II crystal structure by using an aqueous sulfuric acid solution as a sulfating reagent (for example, Patent Literature 2).

In Patent Literature 1, although the sulfated cellulose maintains the granular form, there is a concern about a decrease in the degree of polymerization due to the use of sulfuric acid anhydride, which has a high acidity. In Patent Literature 2, since an aqueous sulfuric acid solution having a high concentration is used, the sulfated cellulose dissolves into cellulose molecules and is transformed into the cellulose II crystal structure, and furthermore, the degree of polymerization is as low as about 60. Therefore, sufficient thickening properties and reinforcing properties are not obtained.

For the reasons described above, to date, there has been no sulfated cellulose fiber that has the cellulose I crystal structure and that maintains a fiber length.

CITATION LIST

Patent Literature

PTL 1: Japanese Unexamined Patent Application Publication No. 2007-92034

PTL 2: Japanese Unexamined Patent Application Publication (Translation of PCT Application) No. 2012-526156

SUMMARY OF INVENTION

Technical Problem

An object of embodiments of the present invention is to provide a sulfated cellulose fiber.

Solution to Problem

Embodiments of the present invention relate to [1] and [2] described below.

[1] A chemically modified cellulose fiber which has a cellulose I crystal and in which some hydroxyl groups of cellulose are substituted with a substituent represented by structural formula (1) below:

[Chem. 1]

(1)

(where M represents a monovalent to trivalent cation) wherein an amount of the substituent introduced is 0.1 mmol to 3.0 mmol per 1 g of the chemically modified cellulose fiber, and an average degree of polymerization is 350 or more.

[2] A method for producing the chemically modified cellulose fiber according to [1] above, the method including a step of treating a cellulose fiber with sulfamic acid while maintaining a cellulose fiber shape to allow sulfamic acid and a cellulose fine fiber which is a constituent of the cellulose fiber to react with each other, thereby subjecting the cellulose fine fiber to sulfation.

Advantageous Effects of Invention

According to the embodiments, it is possible to provide a sulfated cellulose fiber that has the cellulose I crystal structure and that maintains a fiber length.

DESCRIPTION OF EMBODIMENTS

[Chemically Modified Cellulose Fiber]

Chemically modified cellulose fibers according to the present embodiment are each a chemically modified cellulose fiber which has a cellulose I crystal and in which some hydroxyl groups in a glucose unit constituting cellulose are substituted with a substituent represented by formula (1) below.

[Chem. 2]

(1)

In the formula, M represents a monovalent to trivalent cation.

(Cellulose I Crystal)

The chemically modified cellulose fibers have a cellulose I crystal structure, and the degree of crystallinity thereof is preferably 50% or more. When the degree of crystallinity is 50% or more, characteristics derived from the cellulose crystal structure can be exhibited to improve thickening properties and mechanical strength. The degree of crystallinity is more preferably 60% or more, still more preferably 65% or more, and may be 70% or more. The upper limit of the degree of crystallinity is not particularly limited. From the viewpoint of improving the reaction efficiency of sulfation reaction, the degree of crystallinity is preferably 98% or less, more preferably 95% or less, still more preferably 90% or less, and may be 85% or less.

Herein, the degree of crystallinity of cellulose refers to a degree of cellulose I crystallinity calculated by using the Segal method from diffraction intensity values by X-ray diffractometry and is defined by the following equation.
Degree of cellulose I crystallinity (%)=$[(I_{22.6}-I_{18.5})/I_{22.6}] \times 100$ In the equation, $I_{22.6}$ represents a diffraction intensity of a lattice plane (002 plane) (diffraction angle 2θ=22.6°), and $I_{18.5}$ represents a diffraction intensity of an amorphous portion (diffraction angle 2θ=18.5°) in X-ray diffraction. Note that cellulose I refers to a crystal form of natural cellulose, and the degree of cellulose I crystallinity means a ratio of an amount of crystal region to a total amount of cellulose.

(Substituent)

The substituent represented by formula (1) above is a sulfate group. As shown by the formula below, the substituent has a structure in which, instead of a hydrogen atom, —$SO_3^-M$ is bound to an oxygen atom of a hydroxyl group in cellulose where the wavy line portion represents a cellulose molecule, and thus the sulfate group is introduced into a cellulose fiber.

[Chem. 3]

Examples of the monovalent to trivalent cation represented by M in formula (1) include a hydrogen ion, metal ions, and ammonium ions. In the case of a divalent or trivalent cation, the cation forms ionic bonds between the cation and two or three —$OSO_3^-$.

Examples of the metal ions include alkali metal ions, alkaline earth metal ions, transition metal ions, and other metal ions. Here, examples of the alkali metal include lithium, sodium, potassium, rubidium, and cesium. Examples of the alkaline earth metal include calcium and strontium. Examples of the transition metal include iron, nickel, palladium, copper, and silver. Examples of the other metal include beryllium, magnesium, zinc, and aluminum.

The ammonium ions include not only $NH_4^+$ but also ammonium ions derived from various amines formed by replacing at least one hydrogen atom of $NH_4^+$ with an organic group. Examples thereof include $NH_4^+$, quaternary ammonium cations, alkanolamine ions, and a pyridinium ion.

The cation represented by M is preferably a sodium ion, a potassium ion, a calcium ion, or a quaternary ammonium cation from the viewpoint of storage stability. The cations listed above may be any one or a combination of two or more thereof.

(Amount of Substituent Introduced)

In the chemically modified cellulose fibers, an amount of the substituent represented by formula (1) above and introduced per 1 g of the chemically modified cellulose fibers is preferably 0.1 to 3.0 mmol. When the amount introduced is 3.0 mmol/g or less, the effect of maintaining the cellulose crystal structure can be enhanced. The amount introduced is more preferably 2.8 mmol/q or less, still more preferably 2.5 mmol/g or less. The amount introduced is preferably 0.1 mmol/g or more, more preferably 0.15 mmol/q or more, still more preferably 0.2 mmol/g or more from the viewpoint of covering, with the substituent, the entire surfaces of cellulose fine fibers which are a constituent of cellulose fibers.

Herein, the amount of substituent introduced is a value calculated by potentiometry. For example, the amount of substituent can be calculated by removing, by washing, a modifying agent used as a raw material and by-products such as hydrolysate of the modifying agent, and subsequently conducting analysis by potentiometry. The amount of substituent can be specifically measured by the method described in Examples below.

(Average Degree of Polymerization)

The average degree of polymerization (that is, the number of repetitions of a glucose unit) of the chemically modified cellulose fibers is preferably 350 or more. When the average degree of polymerization is 350 or more, thickening properties can be improved. The average degree of polymerization is more preferably 380 or more, still more preferably 400 or more. The upper limit of the average degree of polymerization is not particularly limited and may be, for example, 5,000 or less, 4,000 or less, 3,000 or less, and 2,000 or less.

Herein, the average degree of polymerization is a value measured by a viscosity method and can be specifically measured by the method described in Examples below.

(Average Fiber Width and Average Fiber Length)

Examples of the chemically modified cellulose fibers according to the present embodiment include micrometer-sized chemically modified cellulose fibers (form 1) that have not been subjected to a fibrillation process (miniaturization process) and nanometer-sized chemically modified cellulose fibers (form 2) that have been subjected to a fibrillation process.

The average fiber width of the chemically modified cellulose fibers of form 1 is preferably more than 5 μm, more preferably 8 μm or more, and still more preferably 10 μm or more from the viewpoint of maintaining the pulp form (that is, cellulose fiber shape serving as a cellulose raw material). The upper limit of the average fiber width is not particularly limited but is preferably 100 μm or less, more preferably 80 μm or less, still more preferably 60 μm or less in consideration of the form of the cellulose raw material.

The average fiber length of the chemically modified cellulose fibers of form 1 is preferably 0.5 mm or more, more preferably 0.8 mm or more, still more preferably 1.0 mm or more from the viewpoint of enhancing thickening properties and mechanical strength. The upper limit of the average fiber length is not particularly limited but is preferably 50 mm or less, more preferably 30 mm or less, still more preferably 10 mm or less in consideration of the form of cellulose raw material.

A part of the chemically modified cellulose fibers of form 1 may become fibrillated because the substituent represented by formula (1) above is hydrophilic.

The chemically modified cellulose fibers of form 2 are fine chemically modified cellulose fibers that have been subjected to a fibrillation process and, therefore, can be referred to as chemically modified fibrillated cellulose fibers or chemically modified cellulose fine fibers. The average fiber width of the chemically modified cellulose fibers of form 2 is preferably 3 nm or more, more preferably 5 nm or more, still more preferably 8 nm or more, and may be 10 nm or more, and 30 nm or more from the viewpoint of producing fine chemically modified cellulose fibers that maintain the cellulose I crystal structure. The average fiber width is preferably 5 µm or less, more preferably 1 µm or less, still more preferably 0.5 µm or less, even still more preferably 0.1 µm or less from the viewpoint of obtaining pure chemically modified cellulose fibers by removing other constituents of pulp (such as bordered pits and vessel elements) at the stage of producing chemically modified cellulose fibers.

The average fiber length of the chemically modified cellulose fibers of form 2 is preferably 0.1 µm or more, more preferably 1 µm or more, still more preferably 10 µm or more from the viewpoint of enhancing thickening properties and mechanical strength. The upper limit of the average fiber length is not particularly limited, but is preferably 500 µm or less, and may be 300 µm or less and 200 µm or less.

Herein, the average fiber width and the average fiber length of chemically modified cellulose fibers are respectively the averages of fiber widths and fiber lengths of 50 fibers measured by microscopic observation and are specifically measured by the method described in Examples below.

[Method for Producing Chemically Modified Cellulose Fiber]

A method for producing a chemically modified cellulose fiber according to one embodiment is a method for producing a chemically modified cellulose fiber by allowing a cellulose fiber and sulfamic acid to react with each other. The method includes a step (chemical modification step) of treating a cellulose fiber with sulfamic acid while maintaining a cellulose fiber shape to allow the sulfamic acid and a cellulose fine fiber which is a constituent of the cellulose fiber to react with each other, thereby subjecting the cellulose fine fiber to sulfation.

Through this chemical modification step, the micrometer-sized chemically modified cellulose fibers according to form 1 are produced. Furthermore, a step (miniaturization step) of mechanically fibrillating the chemically modified cellulose fibers (form 1) obtained by the chemical modification step may be performed. Mechanical fibrillation of the chemically modified cellulose fibers of form 1 can provide the nanometer-sized chemically modified cellulose fibers according to form 2.

(Cellulose Raw Material)

Specific examples of the cellulose fiber (cellulose raw material) used in the chemical modification step include cellulose fibers derived from origins such as plants (e.g., wood, cotton, bamboo, hemp, jute, kenaf, agricultural land residual wastes, cloth, pulp, regenerated pulp, and wastepaper); animals (e.g., sea squirt); algaes; microorganisms (e.g., *acetobacter*); and microorganism products. Among these, pulp derived from plants is a preferred raw material.

The pulp is preferably chemical pulp (kraft pulp (KP) or sulfite pulp (SP)), semi-chemical pulp (SCP), chemiground pulp (CGP), chemimechanical pulp (CMP), groundwood pulp (GP), refiner mechanical pulp (RMP), thermomechanical pulp (TMP), or chemithermomechanical pulp (CTMP), which can be produced by chemical or mechanical pulping or combination of chemical and mechanical pulping of the plant raw material.

The cellulose raw material may be chemically modified within a range that does not impair the object of the present embodiment. Specifically, chemically modified pulp may be used. For example, the cellulose raw material can include an esterified product in which some or most of hydroxyl groups present on the surface of a cellulose fiber or the surface of a cellulose fine fiber each include an acetic acid ester or a nitric acid ester; an etherified product in which some or most of hydroxyl groups present on the surface of a cellulose fiber or the surface of a cellulose fine fiber each include methyl ether, hydroxyethyl ether, hydroxypropyl ether, hydroxybutyl ether, carboxymethyl ether, or cyanoethyl ether; or TEMPO-oxidized pulp in which primary hydroxyl groups are oxidized.

A cellulose raw material which has a cellulose I crystal and in which the crystal has a degree of crystallinity of 50% or more is preferably used. The value of the degree of cellulose I crystallinity of the cellulose raw material is more preferably 60% or more, still more preferably 70% or more. The upper limit of the degree of cellulose I crystallinity of the cellulose raw material is not particularly limited but may be 98% or less, 95% or less, and 90% or less.

The form of the cellulose raw material used in the present embodiment is not particularly limited. However, from the viewpoint of handleability, the cellulose raw material preferably has a fiber form, a sheet form, a flocculent form, a powder form, a chip form, or a flake form.

(Pretreatment Step)

In the case of using a cellulose raw material having a bulk density of 10 kg/m$^3$ or more, a pretreatment step may be performed prior to the reaction in the chemical modification step so that the bulk density is adjusted to 0.1 to 5 kg/m$^3$. This pretreatment performed in advance enables chemical modification to be more efficiently performed. The pretreatment is not particularly limited. However, the bulk density of the cellulose raw material can be adjusted to a suitable value by a mechanical process. The machine and processing conditions used in the mechanical process are not limited. Examples of the machine include shredders, ball mills, vibrating mills, stone mills, grinders, blenders, and high-speed rotary mixers. The bulk density is preferably 0.1 to 5.0 kg/m$^3$, more preferably 0.1 to 3.0 kg/m$^3$, still more preferably 0.1 to 1.0 kg/m$^3$.

(Reaction Step)

In the chemical modification step, the reaction between a cellulose fiber and sulfamic acid (that is, sulfation reaction) can be conducted by immersing a cellulose raw material (cellulose fibers) in a chemical liquid that contains sulfamic acid.

In the present embodiment, it is preferable to chemically modify, with sulfamic acid, the surfaces of cellulose fine fibers, which are a constituent of cellulose fibers, while maintaining the shape of the cellulose fibers. Specifically, cellulose fibers are each formed of a bundle of cellulose fine fibers (also referred to as cellulose nanofibers) which are a constituent of the cellulose fibers. In the present embodiment, the surfaces of the cellulose fine fibers are preferably chemically modified with sulfamic acid while maintaining the shape of cellulose fibers each of which is formed of a bundle of cellulose fine fibers (that is, without fibrillation). Since the esterification process is performed in the state where cellulose fibers are not fibrillated, an increase in the viscosity of the cellulose fiber dispersion liquid is suppressed, and efficiency and productivity can be improved. Note that even if a part of the chemically modified cellulose fibers becomes fibrillated as described above, the chemically modified cellulose fibers are not substantially fibrillated as long as the state of the bundle of cellulose fine fibers is maintained on the whole. Accordingly, the cellulose fiber shape is considered to be maintained. Thus, the above case is also included in the production method according to the present embodiment.

Sulfamic acid is preferably used as the sulfating reagent. Sulfamic acid has not only low cellulose solubility but also low acidity compared with sulfuric acid anhydride, an aqueous sulfuric acid solution, and the like, and thus the degree of polymerization can be maintained. In contrast to sulfuric acid anhydride and an aqueous sulfuric acid solution, which are strongly acidic and have high corrosiveness, sulfamic acid does not have limitation in terms of handling and is not designated as a substance specified by the air pollution control law. Therefore, sulfamic acid has low load on the environment.

The amount of sulfamic acid used can be appropriately adjusted in consideration of the amount of the substituent introduced into cellulose fibers. Sulfamic acid can be used, for example, in an amount of preferably 0.01 to 50 moles, more preferably 0.1 to 30 moles per one mole of the anhydroglucose unit in cellulose molecules.

The chemical liquid used for conducting the sulfation reaction is a mixture of sulfamic acid and a solvent, and a catalyst may be optionally added to the chemical liquid. Examples of the catalyst include urea, amides, and tertiary amines. From the industrial viewpoint, urea is preferably used. The amount of catalyst used is not particularly limited but is preferably 0.001 to 5 moles, more preferably 0.005 to 2.5 moles, still more preferably 0.01 to 2.0 moles per one mole of the anhydroglucose unit in cellulose molecules. A catalyst having a high concentration may be used without further treatment or may be diluted with a solvent in advance and then used. The method for adding the basic catalyst is not particularly limited. The catalyst may be added in a single operation, in batches, or on a continuous basis. These methods may be used in combination. However, it is preferable not to use a catalyst during the reaction from the viewpoint of environmental load and the industrial viewpoint.

The solvent used in the chemical liquid is not particularly limited, and known solvents may be used. Examples of the known solvents include, besides water, linear or branched alcohols having 1 to 12 carbon atoms, such as methanol, ethanol, propanol, butanol, octanol, and dodecanol; ketones having 3 to 6 carbon atoms, such as acetone, methyl ethyl ketone, and methyl isobutyl ketone; linear or branched saturated hydrocarbons and unsaturated hydrocarbons having 1 to 6 carbon atoms; aromatic hydrocarbons such as benzene and toluene; halogenated hydrocarbons such as methylene chloride and chloroform; lower alkyl ethers having 2 to 5 carbon atoms; dioxane, acetonitrile, N,N-dimethylformamide, N,N-dimethylacetamide, dimethyl sulfoxide, N-methylpyrrolidone, and pyridine. These solvents may be used alone or as a mixture of two or more thereof. Among the above solvents, for example, water or a polar organic solvent is more preferred from the viewpoint of accelerating swelling of the cellulose raw material. The above solvents may be used alone or in combination of two or more thereof. The amount of solvent used is not particularly limited. For example, the solvent is used so that a solvent content of the cellulose raw material (that is, a ratio of the mass of the solvent to the dry mass of the cellulose raw material) is 10% by mass or more, preferably 10% by mass to 10,000% by mass, more preferably 20% by mass to 5,000% by mass, still more preferably 50% by mass to 2,000% by mass. With a decrease in the amount of solvent, the convenience of a washing step improves.

The temperature of the sulfation reaction is 0° C. to 100° C., preferably 10° C. to 80° C., more preferably 20° C. to 70° C. An excessively low reaction temperature is not preferred because it takes a long time to complete the reaction. An excessively high reaction temperature is not preferred because glycosidic bonds in cellulose molecules are cleaved. The sulfation reaction is usually completed within 30 minutes to 5 hours.

In order to obtain a product with less coloring, an inert gas such as nitrogen gas, neon gas, argon gas, or helium gas or carbon dioxide may be introduced during the sulfation reaction. The method for introducing the inert gas may be any of a method in which the reaction is performed while blowing the inert gas into a reaction vessel, a method in which the inside of a reaction vessel is purged with the inert gas prior to the reaction, the reaction vessel is then sealed and the reaction is performed, and other methods. However, it is preferable not to use a gas during the reaction from the industrial viewpoint.

(Neutralization/Washing Step)

In the present embodiment, a step of neutralizing a sulfate salt may be performed as required. In the case where the pH of the resulting crude product of a sulfate salt decreases and acidity is exhibited, the crude product has low storage stability. Therefore, it is preferable to adjust the pH value to a neutral or alkaline range by adding a basic compound to the sulfate salt to neutralize the sulfate salt. Examples of the basic compound used for neutralization include, but are not particularly limited to, alkali metal hydroxides, alkaline earth metal hydroxides, other inorganic salts, and amines. Specific examples thereof include sodium hydroxide, potassium hydroxide, calcium hydroxide, calcium acetate, calcium lactate, calcium oxalate, magnesium hydroxide, magnesium acetate, magnesium lactate, magnesium oxalate, basic aluminum lactate, basic aluminum chloride, ammonia, methylamine, dimethylamine, trimethylamine, triethylamine, monoethanolamine, diethanolamine, and triethanolamine. In the present embodiment, the neutralization can be performed by using one or more basic compounds.

In addition, a step of washing chemically modified cellulose fibers in a wet state may be performed for the purpose of terminating the reaction and/or removing a sulfating reagent residue, a residual catalyst, a solvent, etc. In this case, washing conditions are not particularly limited, but the chemically modified cellulose fibers after the completion of the reaction are preferably washed with an organic solvent.

The method for removing the solvent is not particularly limited but a centrifugal sedimentation method, filtration, a press process, or the like can be employed. Here, a sheet formed of chemically modified cellulose fibers may remain in a wet state with an organic solvent without completely removing the organic solvent. An organic solvent content of the chemically modified cellulose fibers (that is, a ratio of the mass of the organic solvent to the dry mass of the chemically modified cellulose fiber assembly) is preferably 1% by mass to 500% by mass, more preferably 10% by mass to 100% by mass, still more preferably 10% by mass to 50% by mass.

(Chemically Modified Cellulose Fiber)

Through the steps described above, the micrometer-sized chemically modified cellulose fibers according to form 1 are produced. In the resulting chemically modified cellulose fibers, some hydroxyl groups in cellulose are substituted with the sulfate group represented by formula (1), and the cellulose fibers are thereby sulfated. That is, in the chemically modified cellulose fibers obtained at this stage, cellulose fine fibers, which are a constituent of cellulose fibers, have been subjected to sulfation by the sulfate group represented by formula (1), and the chemically modified cellulose fibers are constituted by the cellulose fine fibers that have been subjected to sulfation. The sulfate group is introduced on the surfaces of the cellulose fine fibers constituting each cellulose fiber. The sulfate group is preferably introduced not only on the surfaces of cellulose fine fibers that are present on the surface of a cellulose fiber but also on the surfaces of cellulose fine fibers that are present inside the cellulose fiber.

The chemically modified cellulose fibers can be dispersed in an organic solvent. A chemically modified cellulose fiber dispersion can be obtained in which the chemically modified cellulose fibers are dispersed in the organic solvent. Examples of the stirring device include, but are not particularly limited to, a stirrer, a blender, and a homomixer. The concentration of the chemically modified cellulose fiber dispersion (slurry concentration) is not particularly limited as long as stirring can be performed but is preferably 0.01% by mass to 5% by mass.

(Miniaturization Step)

A miniaturization process of the chemically modified cellulose fibers of form 1 by mechanical fibrillation enables the production of the nanometer-sized chemically modified cellulose fibers according to form 2. Examples of the device for performing the miniaturization process of the chemically modified cellulose fibers include refiners, twin-screw kneaders (twin-screw extruders), high-pressure homogenizers, medium stirring mills (such as rocking mills, ball mills, and bead mills), stone mills, grinders, vibrating mills, and sand grinders. The chemically modified cellulose fibers may be made commercially available without performing this miniaturization step.

[Operation and Effect/Use]

The chemically modified cellulose fibers according to the present embodiment have cellulose surfaces that have been subjected to sulfation, and thus can be used as a thickener or a water-absorptive material. The chemically modified cellulose fibers can be used in, for example, industrial raw materials of food, cosmetics, functional paper, resin reinforcing materials, etc., and various other applications. Furthermore, since the chemically modified cellulose fibers according to the present embodiment have a high degree of polymerization, have the cellulose I crystal structure, and maintain the fiber length, the chemically modified cellulose fibers have high thickening properties. In particular, the chemically modified cellulose fibers after fibrillation according to form 2 significantly achieve this effect.

The present embodiment is industrially advantageous in that sulfated cellulose fibers can be efficiently produced with environmental suitability at high productivity. In more detail, chemically modified cellulose fibers can be produced at a low cost while reducing the environmental load by allowing cellulose fibers and sulfamic acid to react with each other.

Since the chemical modification step described above enables chemically modified cellulose fibers to be provided while maintaining the fiber shape, chemically modified cellulose fibers can be efficiently produced at high productivity. The resulting chemically modified cellulose fibers can be easily dispersed in water and can be easily made finer by the fibrillation process, and thus the fibrillation process can be performed by the user. Therefore, chemically modified cellulose fibers before the miniaturization process may be made commercially available at this stage and supplied to the user. For example, the chemically modified cellulose fibers may be supplied to the user in the form of a sheet, and the distribution cost can be thereby reduced.

EXAMPLES

Hereafter, the present invention will be described in more detail by way of Examples. However, the present invention is not limited to the Examples. Measurement/evaluation methods in Examples and Comparative Examples are as follows.

(1) Degree of Cellulose I Crystallinity

The X-ray diffraction intensities of a cellulose raw material and a chemically modified cellulose fiber were measured by X-ray diffractometry. The degree of cellulose I crystallinity was calculated from the measurement results by the following equation using the Segal method.

$$\text{Degree of cellulose } I \text{ crystallinity (\%)} = [(I_{22.6} - I_{18.5})/I_{22.6}] \times 100$$

In the equation, $I_{22.6}$ represents a diffraction intensity of a lattice plane (002 plane) (diffraction angle $2\theta = 22.6°$), and $I_{18.5}$ represents a diffraction intensity of an amorphous portion (diffraction angle $2\theta = 18.5°$) in X-ray diffraction. The X-ray diffraction intensities of samples were measured using "RINT2200" manufactured by Rigaku Corporation under the following conditions:

X-ray source: Cu/Kα-radiation
Tube voltage: 40 kV
Tube current: 30 mA
Measurement range: diffraction angle $2\theta = 5°$ to $35°$
X-ray scan speed: 10°/min.

(2) Identification of Chemically Modified Cellulose Fiber

A group (substituent) introduced in chemically modified cellulose fibers was identified with a Fourier transform infrared spectrophotometer (FT-IR, ATR method).

(3) Measurement of Amount of Substituent Introduced in Chemically Modified Cellulose Fiber The amount of substituents (sulfate groups) introduced was calculated by potentiometry. More specifically, 60 mL of a water dispersion of chemically modified cellulose fibers, the water dispersion having an adjusted solid content of 0.5% by mass, was prepared from a chemically modified cellulose fiber sample whose dry weight had been precisely weighed. The pH of the water dispersion was adjusted to about 2.0 with a 0.1 M aqueous hydrochloric acid solution. Subsequently, the resulting dispersion was filtered, and the fibers were washed with water. The fibers were again dispersed in 60 mL of water, and electrical conductivity was measured by adding dropwise a 0.1 M aqueous potassium hydroxide solution. The measurement was continued until the pH reached 11. The amount of sulfate groups introduced was calculated from an amount of potassium hydroxide consumed in a weak acid neutralization stage in which the electrical conductivity is gently changed.

(4) Measurement of Average Degree of Polymerization of Chemically Modified Cellulose Fiber (Viscosity Method)

The average degree of polymerization of chemically modified cellulose fibers was calculated by a viscosity method. The limiting viscosity number [η] was measured in accordance with JIS-P8215, and the average degree of polymerization (DP) was determined by the following equation.

$$DP = (1/Km) \times [\eta]$$

(Km represents a coefficient and is a value specific to cellulose. $1/Km = 156$)

(5) Fiber Shape Evaluation of Chemically Modified Cellulose Fiber

In chemically modified cellulose fibers before fibrillation, the shape of the chemically modified cellulose fibers was evaluated by optical microscopy in accordance with the following criteria.

AA: The fiber shape is maintained.

A: The fiber shape is maintained, and the fibers are partially fibrillated.

B: The fiber shape is maintained, but the fibers are partially cut.

C: The fiber shape is not maintained, and the fibers are dissolved or shortened.

(6) Measurement of Average Fiber Width and Average Fiber Length of Chemically Modified Cellulose Fiber The average fiber width and the average fiber length of chemically modified cellulose fibers after chemical modification (that is, before fibrillation) were measured by optical microscopy. The averages of fiber widths and fiber lengths of 50 fibers observed at a magnification of 100 to 400 were calculated and defined as the average fiber width and the average fiber length, respectively.

On the other hand, the average fiber width and the average fiber length of chemically modified cellulose fibers after the miniaturization step (that is, after fibrillation) were measured with a scanning electron microscope (SEM). Wet chemically modified cellulose fibers were filtered to remove a solvent. Thus, a fine fiber sheet was prepared. The fine fiber sheet was freeze-dried in liquid nitrogen and observed with a SEM. The averages of fiber widths and fiber lengths of 50 fibers observed at a magnification of 100 to 10,000 were calculated and defined as the average fiber width and the average fiber length, respectively.

(7) Evaluation of Water Dispersibility

With regard to chemically modified cellulose fibers before and after fibrillation, a water dispersion of the chemically modified cellulose fibers, the water dispersion having an adjusted solid content of 0.2% by mass, was allowed to stand for one night. The state of the fibers was then visually observed and evaluated in accordance with the following criteria.

A: The fibers are dispersed in water.

B: The fibers are swollen in water.

C: The fibers are aggregated in water.

(8) Measurement of Viscosity

A viscosity of a water dispersion of chemically modified cellulose fibers, the water dispersion having an adjusted solid content of 0.5% by mass, was measured by using a B-type viscometer at a number of rotations of 6.0 rpm at 25° C. for 3 minutes.

Example 1

(Chemical Modification Step)

In a separable flask, 3.0 g of sulfamic acid and 50 g of N,N-dimethylformamide (DMF) were placed, and stirring was performed for 10 minutes. Subsequently, 1.0 g of flocculent softwood kraft pulp (NBKP, degree of cellulose I crystallinity: 85%) was placed as a cellulose raw material at room temperature. Here, the amount of sulfamic acid used as a sulfating reagent was 5.2 moles per one mole of the anhydroglucose unit in cellulose molecules. The resulting mixture was allowed to react at 50° C. for three hours and then cooled to room temperature. Next, the resulting chemically modified cellulose fibers were taken out and placed in a 2 N aqueous sodium hydroxide solution serving as a neutralizer. The pH was adjusted to 7.6, and the reaction was terminated. The resulting chemically modified cellulose fibers were washed with water two to three times and then centrifuged. Thus, chemically modified cellulose fibers were prepared (amount of solid: 1.24 g, solid content: 6.4% by mass).

(Miniaturization Step)

The chemically modified cellulose fibers prepared above were diluted so as to have a solid content of 5.0% by mass. The resulting water dispersion of the chemically modified cellulose fibers was placed in a zirconia container (volume: 1 L, diameter: 10 cm) filled with zirconia beads (20 mm in diameter: 30 beads, 10 mm in diameter: 100 beads). The container was rotated (rotated on the axis thereof) at room temperature at 60 rpm to perform a ball mill process for two hours. Subsequently, the water dispersion was diluted with water so as to have a solid content of 0.5% by mass and subjected to a process with a microfluidizer (at 150 MPa, 1 pass). Thus, a water dispersion of chemically modified cellulose fine fibers was prepared (amount of solid: 1.12 g, solid content: 0.5% by mass).

Example 2

The reaction, the washing, the solvent removal process, and the miniaturization process were performed as in Example 1 except that, in Example 1, the amount of sulfamic acid charged in the chemical modification step was 0.7 g, the amount of DMF charged was 14 g, the reaction was performed at 25° C. for 24 hours, and no neutralizer was used.

Example 3

The reaction, the washing, the solvent removal process, and the miniaturization process were performed as in Example 1 except that, in Example 1, the amount of sulfamic acid charged in the chemical modification step was 3.8 g, the reaction was performed at 50° C. for three hours, and only the ball mill process was performed in the miniaturization step under the same conditions as those in Example 1.

Example 4

The reaction, the washing, the solvent removal process, and the miniaturization process were performed as in Example 1 except that, in Example 1, the amount of sulfamic acid charged in the chemical modification step was 3.8 g, the reaction was performed at 50° C. for five hours, and only the microfluidizer process was performed in the miniaturization step under the same conditions as those in Example 1.

Example 5

The reaction, the washing, the solvent removal process, and the miniaturization process were performed as in Example 1 except that, in Example 1, the amount of sulfamic acid charged in the chemical modification step was 1.1 g, 1.1 g of urea was added as a catalyst, the amount of DMF charged was 14 g, monoethanolamine was used as a neutralizer, and only the ball mill process was performed in the miniaturization step under the same conditions as those in Example 1.

Example 6

The reaction, the washing, the solvent removal process, and the miniaturization process were performed as in Example 1 except that, in Example 1, the amount of sulfamic acid charged in the chemical modification step was 0.35 g, the amount of DMF charged was 14 g, 1.5 g of pyridine (the cation of which is a pyridinium ion) was added as a catalyst, pyridine was used as a neutralizer, and only the ball mill process was performed in the miniaturization step under the same conditions as those in Example 1.

Comparative Example 1

The reaction, the washing, the solvent removal process, and the miniaturization process were performed as in Example 1 except that, in Example 1, 1.5 g of sulfur trioxide was used instead of sulfamic acid in the chemical modification step, the amount of DMF charged was 20 g, and the reaction was performed at 40° C. for five hours.

Comparative Example 2

The reaction and the neutralization process were performed as in Example 1 except that, in Example 1, the reaction in the chemical modification step was performed at 60° C. for five hours. Since the resulting chemically modified cellulose fibers were soluble in water, the miniaturization process was not performed.

Comparative Example 3

As a cellulose raw material, 1.0 g of flocculent softwood kraft pulp (NBKP, degree of cellulose I crystallinity: 85%) was dispersed in water, and the resulting dispersion was diluted so as to have a solid content of 5.0% by mass. The resulting water dispersion of cellulose fibers was subjected to the ball mill process under the same conditions as those in Example 1. Subsequently, washing was performed with water, and centrifugal separation was performed. Thus, a water dispersion of cellulose fibers was prepared.

With regard to the chemically modified cellulose fibers after the chemical modification step in Examples and Comparative Examples described above, the identification of the group introduced, the calculations of the amount of the group introduced, the average degree of polymerization, and the degree of crystallinity, the evaluation of the fiber shape, the measurement of the average fiber width and the average fiber length, and the evaluation of water dispersibility were performed. Furthermore, with regard to the fibers after the miniaturization step, the measurement of the average fiber width and the average fiber length, the evaluation of water dispersibility, and the measurement of the viscosity were performed. Tables 1 and 2 show the results.

Figure 1:
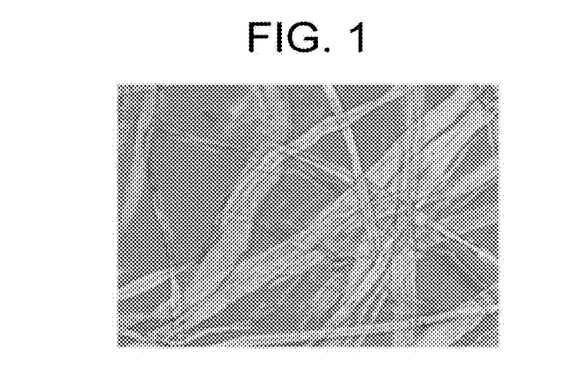
FIG. 1 is an optical micrograph (magnification: 100) of chemically modified cellulose fibers after a chemical modification step, the chemically modified cellulose fibers being produced in Example 1.
Figure 2:
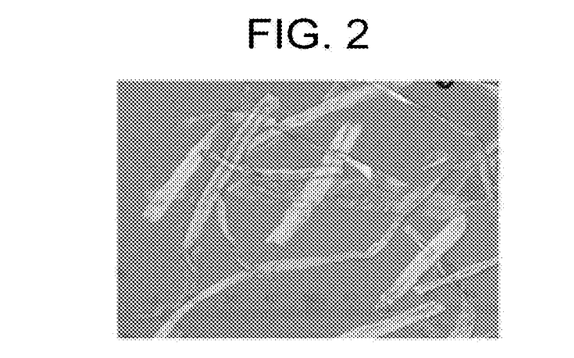
FIG. 2 is an optical micrograph (magnification: 100) of chemically modified cellulose fibers after a chemical modification step, the chemically modified cellulose fibers being produced in Comparative Example 1.
Figure 3:
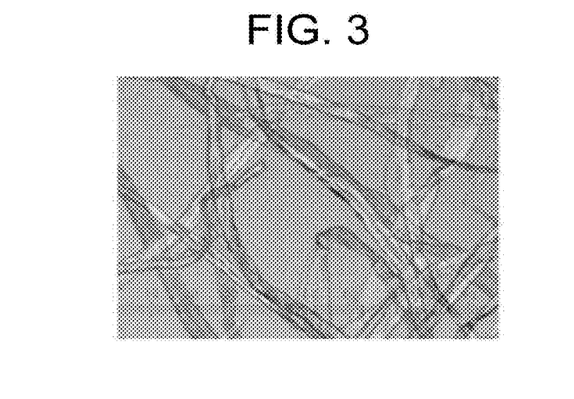
FIG. 3 is an optical micrograph (magnification: 100) of cellulose fibers after a miniaturization step, the cellulose fibers being produced in Comparative Example 3.

FIG. 1 (magnification: 100) is an optical micrograph of the chemically modified cellulose fibers after the chemical modification step, the cellulose fibers being produced in Example 1. FIG. 2 (magnification: 100) is an optical micrograph of the chemically modified cellulose fibers after the chemical modification step, the cellulose fibers being produced in Comparative Example 1. FIG. 3 (magnification: 100) is an optical micrograph of the cellulose fibers after the miniaturization step, the cellulose fibers being produced in Comparative Example 3.

TABLE 1

| | | | Example 1 | Example 2 | Example 3 | Example 4 | Example 5 | Example 6 |
|---|---|---|---|---|---|---|---|---|
| Chemical modification | Cellulose raw material | Type | NBKP | NBKP | NBKP | NBKP | NBKP | NBKP |
| | | Degree of crystallinity [%] | 85 | 85 | 85 | 85 | 85 | 85 |
| | | Amount charged [g] | 1 | 1 | 1 | 1 | 1 | 1 |
| | Reaction solution | Sulfating reagent Type | Sulfamic acid | Sulfamic acid | Sulfamic acid | Sulfamic acid | Sulfamic acid | Sulfamic acid |
| | | Amount charged [g] | 3 | 0.7 | 3.8 | 3.8 | 1.1 | 0.35 |
| | | Catalyst Type | — | — | — | — | Urea | Pyridine |
| | | Amount charged [g] | — | — | — | — | 1.1 | 1.5 |
| | | Solvent Type | DMF | DMF | DMF | DMF | DMF | DMF |
| | | Amount charged [g] | 50 | 14 | 50 | 50 | 14 | 14 |
| | Reaction condition | Temperature [° C.] | 50 | 25 | 50 | 50 | 50 | 50 |
| | | Time [h] | 3 | 24 | 3 | 5 | 3 | 3 |
| | Post-treatment | Neutralizer Type | NaOH | — | NaOH | NaOH | MEA | Pyridine |
| | | Cationic species | $Na^+$ | $NH_4^+$ | $Na^+$ | $Na^+$ | $NH_3^+C_2H_4OH$ | $C_5H_5N^-H$ |
| | Evaluation | Amount introduced [mmol/g] | 0.4 | 0.5 | 0.8 | 2.1 | 1.2 | 0.5 |
| | | Degree of crystallinity [%] | 80 | 78 | 84 | 80 | 73 | 76 |
| | | Average degree of polymerization | 510 | 940 | 1100 | 430 | 920 | 1010 |
| | | Fiber shape evaluation | A | A | A | A | A | A |
| | | Average fiber width [μm] | 35 | 12 | 38 | 26 | 45 | 29 |
| | | Average fiber length [mm] | 3.3 | 2.4 | 4.0 | 2.9 | 5.5 | 4.3 |
| | | Water dispersibility | A | A | A | A | A | A |
| Miniaturization process | Miniaturization process | Solvent Type | Water | Water | Water | Water | Water | Water |
| | | Type | Ball mill → Microfluidizer | Ball mill → Microfluidizer | Ball mill | Microfluidizer | Ball mill | Ball mill |
| | Evaluation | Average fiber width [nm] | 92 | 104 | 3050 | 52 | 460 | 140 |
| | | Average fiber length [μm] | 56 | 52 | 124 | 13 | 267 | 21 |
| | | Water dispersibility | A | A | A | A | A | A |
| | | Viscosity [mPa · s] | 8100 | 6020 | 7200 | 7900 | 6500 | 5400 |

TABLE 2

| | | | Comparative Example 1 | Comparative Example 2 | Comparative Example 3 |
|---|---|---|---|---|---|
| Chemical modification | Cellulose raw material | Type | NBKP | NBKP | NBKP |
| | | Degree of crystallinity [%] | 85 | 85 | 85 |
| | | Amount charged [g] | 1 | 1 | 1 |

TABLE 2-continued

|  |  |  |  | Comparative Example 1 | Comparative Example 2 | Comparative Example 3 |
|---|---|---|---|---|---|---|
|  | Reaction solution | Sulfating reagent | Type | Sulfur trioxide | Sulfamic acid | — |
|  |  |  | Amount charged [g] | 1.5 | 3 | — |
|  |  | Catalyst | Type | — | — | — |
|  |  |  | Amount charged [g] | — | — | — |
|  |  | Solvent | Type | DMF | DMF | — |
|  |  |  | Amount charged [g] | 20 | 50 | — |
|  | Reaction condition | Temperature [° C.] |  | 40 | 60 | — |
|  |  | Time [h] |  | 5 | 5 | — |
|  | Post-treatment | Neutralizer | Type | NaOH | NaOH | — |
|  |  |  | Cationic species | Na+ | Na+ | — |
|  | Evaluation | Amount introduced [mmol/g] |  | 2.3 | 4.5 | 0 |
|  |  | Degree of crystallinity [%] |  | 78 | 56 | 85 |
|  |  | Average degree of polymerization |  | 310 | 405 | 1120 |
|  |  | Fiber shape evaluation |  | C | C | A |
|  |  | Average fiber width [μm] |  | 43 | — | 31 |
|  |  | Average fiber length [mm] |  | 0.32 | — | 3.6 |
|  |  | Water dispersibility |  | C | — | A |
| Miniaturization process | Miniaturization process | Solvent | Type | Water | — | Water |
|  |  | Type |  | Ball mill → Microfluidizer | — | Ball mill |
|  | Evaluation | Average fiber width [nm] |  | 140 | — | >10000 |
|  |  | Average fiber length [μm] |  | 15 | — | 3600 |
|  |  | Water dispersibility |  | B | — | A |
|  |  | Viscosity [mPa · s] |  | (Could not be measured) | — | — |

Details of the components in the tables are as follows.
NBKP: softwood kraft pulp
DMF: dimethylformamide
NaOH: sodium hydroxide
MEA: monoethanolamine The results are as shown in Tables 1 and 2 and FIGS. 1 to 3. In Comparative Example 1, the average degree of polymerization was decreased by sulfur trioxide, which is strongly acidic, and the cellulose fibers were shortened. In addition, the viscosity after the miniaturization process was excessively low and could not be measured. In Comparative Example 2, the degree of crystallinity decreased because of an excessively large amount of sulfate groups introduced. In Comparative Example 3, since no sulfating reagent was used, the cellulose fibers were not chemically modified, and fibrillation by the miniaturization process was insufficient.

In contrast, in Examples 1 to 6, sulfate groups could be introduced on the surfaces of the cellulose fine fibers despite the short-time reaction. The cellulose fibers in Examples 1 to 6 had the cellulose I crystal structure and maintained high degree of crystallinity and high average degree of polymerization. In addition, sulfate groups were introduced while the cellulose fiber shape and the fiber length were maintained. Furthermore, even without using an environmentally toxic sulfating reagent such as sulfur trioxide, sulfation could be easily performed at a low cost by using a reagent having environmental suitability. Since the chemical modification was performed without fibrillation, a high filtrate property was achieved to provide good workability of the washing and the solvent removal process. Consequently, chemically modified cellulose fibers could be efficiently produced at high productivity. The resulting chemically modified cellulose fibers had good dispersibility in water and were easily fibrillated into chemically modified cellulose fine fibers by the miniaturization process. The resulting fine fiber dispersion liquids had high viscosities and exhibited good thickening properties.

Some embodiments of the present invention have been described above. These embodiments are only exemplary and are not intended to limit the scope of the invention. These embodiments can be carried out in various other forms, and various omissions, replacements, and modifications may be made without departing from the spirit of the invention. These embodiments and omissions, replacements, modifications, and the like of the embodiments fall within the scope or spirit of the invention and also fall within the scope of the invention as defined by the appended claims and equivalents thereof.

The invention claimed is:
1. A chemically modified cellulose fiber having a cellulose I crystal structure, comprising:
cellulose fiber comprising cellulose comprising a substituent of structural formula (1),

(1)

where M represents a monovalent to trivalent cation,
wherein the cellulose has the substituent substituting hydroxyl group of the cellulose, and an amount of the substituent is in a range of 0.1 mmol to 3.0 mmol per 1 g of the cellulose fiber, and an average degree of polymerization is 350 or more, and the cellulose fiber has an average fiber width in a range of 3 nm to 5 μm, an average fiber length in a range of 0.1 μm to 500 μm, and a crystallinity of at least 80%.

2. The chemically modified cellulose fiber according to claim 1, wherein the cellulose fiber has an average fiber width in a range of 3 nm to 1 μm.

3. The chemically modified cellulose fiber according to claim 1, wherein the cellulose fiber has an average fiber width in a range of 3 nm to 0.5 µm.

4. The chemically modified cellulose fiber according to claim 1, wherein the cellulose fiber has an average fiber width in a range of 3 nm to 0.1 µm.

5. The chemically modified cellulose fiber according to claim 1, wherein the cellulose fiber has an average fiber width in a range of 5 nm to 1 µm.

6. The chemically modified cellulose fiber according to claim 1, wherein the cellulose fiber has an average fiber width in a range of 8 nm to 0.5 µm.

7. The chemically modified cellulose fiber according to claim 1, wherein the cellulose fiber has an average fiber width in a range of 10 nm to 0.1 µm.

8. The chemically modified cellulose fiber according to claim 1, wherein the cellulose fiber has an average fiber width in a range of 30 nm to 0.1 µm.

9. The chemically modified cellulose fiber according to claim 1, wherein the cellulose fiber has an average fiber length in a range of 1 µm to 300 µM.

10. The chemically modified cellulose fiber according to claim 1, wherein the cellulose fiber has an average fiber length in a range of 10 µm to 200 µm.

11. The chemically modified cellulose fiber according to claim 1, wherein the amount of the substituent is in a range of 0.15 mmol to 2.8 mmol per 1 g of the cellulose fiber.

12. The chemically modified cellulose fiber according to claim 1, wherein the amount of the substituent is in a range of 0.2 mmol to 2.5 mmol per 1 g of the cellulose fiber.

13. The chemically modified cellulose fiber according to claim 1, wherein the average degree of polymerization is in a range of 350 to 5,000.

14. The chemically modified cellulose fiber according to claim 1, wherein the average degree of polymerization is in a range of 380 to 4,000.

15. The chemically modified cellulose fiber according to claim 1, wherein the average degree of polymerization is in a range of 400 to 3,000.

16. The chemically modified cellulose fiber according to claim 1, wherein the cellulose of the cellulose fiber comprises the substituent of structural formula (1), (1)

where M is at least one cation selected from the group consisting of a sodium ion, a potassium ion, a calcium ion and a quaternary ammonium cation.

17. A thickener, comprising:
the chemically modified cellulose fiber of claim 1.

18. A method for producing a chemically modified cellulose fiber, comprising:
treating a cellulose fiber with sulfamic acid while maintaining a cellulose fiber shape such that the sulfamic acid and a cellulose fine fiber of the cellulose fiber react with each other and that the cellulose fine fiber is subjected to sulfation; and
mechanically fibrillating the cellulose fiber such that the cellulose fiber has an average fiber width in a range of 3 nm to 5 µm, an average fiber length in a range of 0.1 µm to 500 µM,
wherein the cellulose fiber has a cellulose I crystal structure and comprises cellulose comprising a substituent of structural formula (1), (1)

where M represents a monovalent to trivalent cation, the cellulose has the substituent substituting hydroxyl group of the cellulose, and an amount of the substituent is in a range of 0.1 mmol to 3.0 mmol per 1 g of the cellulose fiber, and an average degree of polymerization is 350 or more, and the cellulose fiber has a crystallinity of at least 80%.

19. The method for producing the chemically modified cellulose fiber according to claim 18, wherein the cellulose fiber has an average fiber width in a range of 3 nm to 1 µm.

20. The method for producing the chemically modified cellulose fiber according to claim 18, wherein the cellulose fiber has an average fiber width in a range of 3 nm to 0.5 µm.

* * * * *